(12) United States Patent
Quarles et al.

(10) Patent No.: US 12,210,668 B2
(45) Date of Patent: Jan. 28, 2025

(54) SYSTEM AND METHOD FOR PERFORMING PHYSICAL EXAM ON XR-BASED SIMULATED PATIENTS

(71) Applicant: MedCognition, Inc., San Antonio, TX (US)

(72) Inventors: John Quarles, San Antonio, TX (US); Kevin King, San Antonio, TX (US); Sarah Richmond, Redmond, WA (US); Russell Unrath, San Antonio, TX (US)

(73) Assignee: MedCognition, Inc., San Antonio, TX (US)

( * ) Notice: Subject to any disclaimer, the term of this patent is extended or adjusted under 35 U.S.C. 154(b) by 0 days.

(21) Appl. No.: 17/940,322

(22) Filed: Sep. 8, 2022

(65) Prior Publication Data
US 2023/0075639 A1    Mar. 9, 2023

Related U.S. Application Data

(60) Provisional application No. 63/241,907, filed on Sep. 8, 2021.

(51) Int. Cl.
*G06F 3/01* (2006.01)
*G06T 19/00* (2011.01)
*G06V 20/20* (2022.01)
*G06V 40/10* (2022.01)
(Continued)

(52) U.S. Cl.
CPC ............ *G06F 3/011* (2013.01); *G06T 19/006* (2013.01); *G06V 20/20* (2022.01); *G06V 40/10* (2022.01); *G06V 40/28* (2022.01); *G09B 19/00* (2013.01)

(58) Field of Classification Search
CPC ........ G06F 3/011; G06V 20/20; G06V 40/10; G06V 40/28; G06T 19/006; G09B 19/00
See application file for complete search history.

(56) References Cited

U.S. PATENT DOCUMENTS

| | | | |
|---|---|---|---|
| 2017/0213473 A1* | 7/2017 | Ribeira | G09B 5/10 |
| 2018/0256256 A1* | 9/2018 | May | A61F 2/461 |
| 2019/0206134 A1 | 7/2019 | Devam et al. | |

(Continued)

FOREIGN PATENT DOCUMENTS

| | | | | |
|---|---|---|---|---|
| CA | 3167953 A1 * | 8/2021 | | G06F 3/011 |

OTHER PUBLICATIONS

International Search Report and Written Opinion (ISR-WO) issued for International Application No. PCT/US22/42859, mailed Dec. 23, 2022, 7 pages.

(Continued)

*Primary Examiner* — Stephen G Sherman
(74) *Attorney, Agent, or Firm* — Sprinkle IP Law Group (57) ABSTRACT

Systems and methods for medical training are provided. In some embodiments, systems and methods use computer generated simulated patients through augmented reality. In some embodiments, systems and methods enable medical training that allows a user to interact with the simulated patient which provides simulated visual, audio, or other user perceivable reactions. In some embodiments, hand tracking technology is used in a unique way to detect collisions with a virtual object to result in naturally appearing physical exam maneuvers to simulate the physical examination (e.g., auscultation, percussion, palpation stages of a physical examination) of the simulated patient.

20 Claims, 10 Drawing Sheets

(51) Int. Cl.
*G06V 40/20* (2022.01)
*G09B 19/00* (2006.01)

(56) References Cited

U.S. PATENT DOCUMENTS

2020/0286294 A1* 9/2020 Musara .................. G16H 50/30
2020/0333940 A1* 10/2020 Lee ..................... G06F 3/04815

OTHER PUBLICATIONS

International Preliminary Report on Patentability (IPRP) issued by the International Bureau for International Application No. PCT/US22/42859, mailed Mar. 21, 2024, 6 pages.

* cited by examiner

SYSTEM AND METHOD FOR PERFORMING PHYSICAL EXAM ON XR-BASED SIMULATED PATIENTS

CROSS-REFERENCE TO RELATED APPLICATION(S)

This application claims a benefit of priority under 35 U.S.C. § 119(e) from U.S. Provisional Application No. 63/241,907, filed Sep. 8, 2021, entitled "SYSTEM AND METHOD FOR PERFORMING PHYSICAL EXAM ON XR-BASED SIMULATED PATIENTS," which is fully incorporated by reference herein for all purposes.

TECHNICAL FIELD

The present invention relates generally to the field of medical training. More particularly, this disclosure relates to systems and techniques for medical training using computer generated simulated patients, specifically through augmented reality, mixed reality, or virtual reality (XR). In particular, this disclosure relates to systems and methods for medical training that allows a user the interact with a hologram-based simulated patient that provides simulated visual and audio reactions. Even more particularly, the system uses hand tracking technology in a unique way to detect collisions with a virtual object to result in naturally appearing physical exam maneuvers to simulate the physical examination (e.g., auscultation, percussion, palpation stages of a physical examination) of the simulated patient.

BACKGROUND

In medical training, medical personnel must learn to assess patients and make treatment decisions. One critical assessment approach is a physical exam, where the medical personnel must physically touch the patient to assess them. Examples include auscultation (using a stethoscope to listen to the heart, lungs and bowels), palpation (pushing on specific locations on the patient's body), and percussion (tapping on the patient's body to generate a sound).

Current approaches to simulating physical exams include using mechanical mannequins, which are very costly, easy to break, and not very portable. Additionally, mannequins do not automatically respond to palpations or percussion and require an instructor to either trigger the mannequin to respond or narrate the response to the person performing the exam. Other approaches include using an augmented reality display device to display a virtual anatomic display registered with a physical anatomic model. For example, U.S. Pat. No. 10,692,401 describes devices and methods for interactive augmented reality, and is expressly incorporated by reference herein in its entirety.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. The features illustrated in the drawings are not necessarily drawn to scale.

DETAILED DESCRIPTION

The invention and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the invention in detail. It should be understood, however, that the detailed description and the specific examples, while indicating some embodiments of the invention, are given by way of illustration only and not by way of limitation. Various substitutions, modifications, additions and/or rearrangements within the spirit and/or scope of the underlying inventive concept will become apparent to those skilled in the art from this disclosure.

In some embodiments, the invention can be implemented entirely in software. In some embodiments, the invention can use a commercially available augmented reality display device, such as a Microsoft HoloLens™, or other similar device, along with any needed computer or control system, etc. A typical augmented reality device, such as the HoloLens™, will include processor(s)/controllers, memory, operating software, sensors, etc., but can also interface with other computing or control devices, as needed.

The invention enables a medical trainee to reach out and touch a hologram-based simulated patient with their real hands and/or their real hands holding a virtual tool, such as a stethoscope to perform a physical exam. When a user touches the virtual patient at specific locations, the patient will react (e.g., scream and wince in pain in the case of palpations) or will play audio (e.g., the heart, lungs, bowels, or percussion noises, etc. in the case of auscultation). Other virtual patient reactions are also possible.

One advantage of the invention is that a trainee only needs an augmented reality head-mounted display with hand tracking capabilities and the appropriate software to perform a realistic physical exam. No physical mannequin is needed, although a virtual patient can also be projected onto a physical mannequin.

As discussed above, a physical exam may include several stages, as one skilled in the art would understand. For example, a stethoscope can be used to listen to the heart, lungs and bowels (auscultation). An examiner may also push on specific locations on a patient's body to check for tenderness, abnormalities, etc. (palpation). An examiner may also tap on a patient's body to generate a sound in order to assess the structures that lie beneath the skin (percussion).

Following is a description of an example of the operation of the invention when examining a virtual patient using auscultation. In one example, the system uses a virtual stethoscope that is placed in the user's hands as the user conducts an examination. Since the augmented reality system is capable of tracking the user's hands, the system enables the user to move and position the virtual stethoscope on the virtual patient where desired in a natural and clinically intuitive way.

Figure 1:
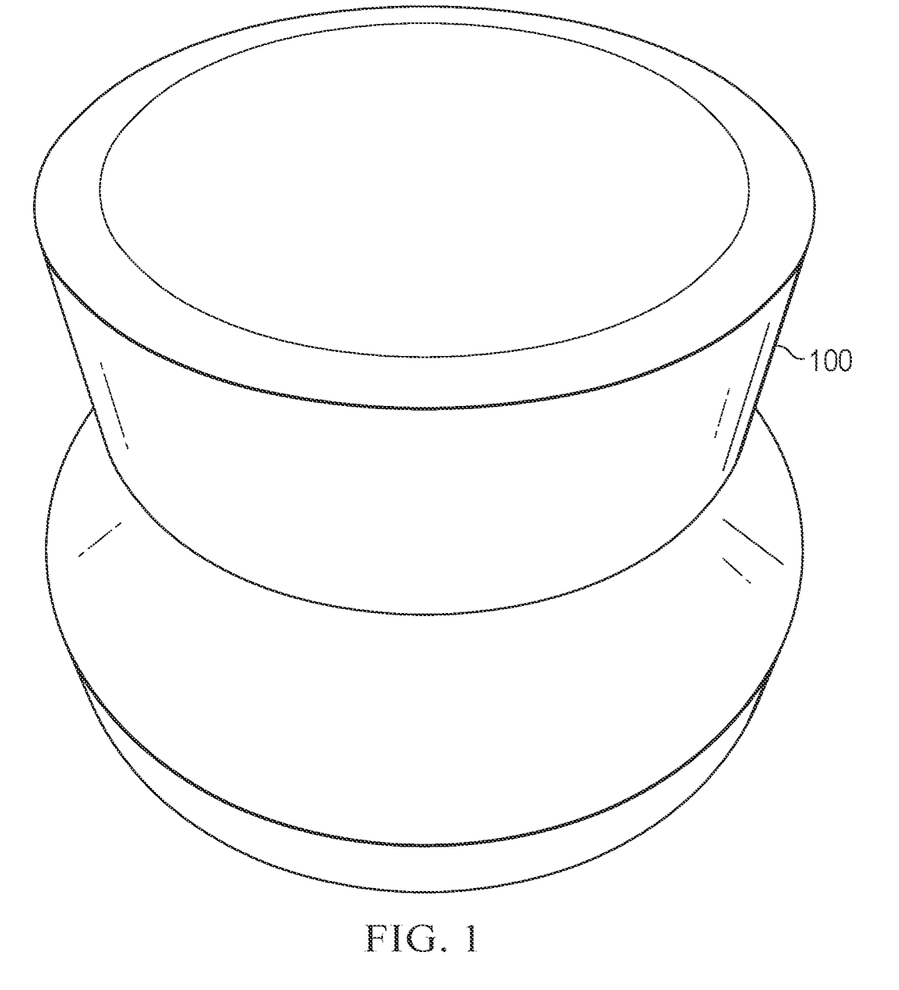
FIG. 1 depicts an example of a virtual stethoscope.
Figure 2:
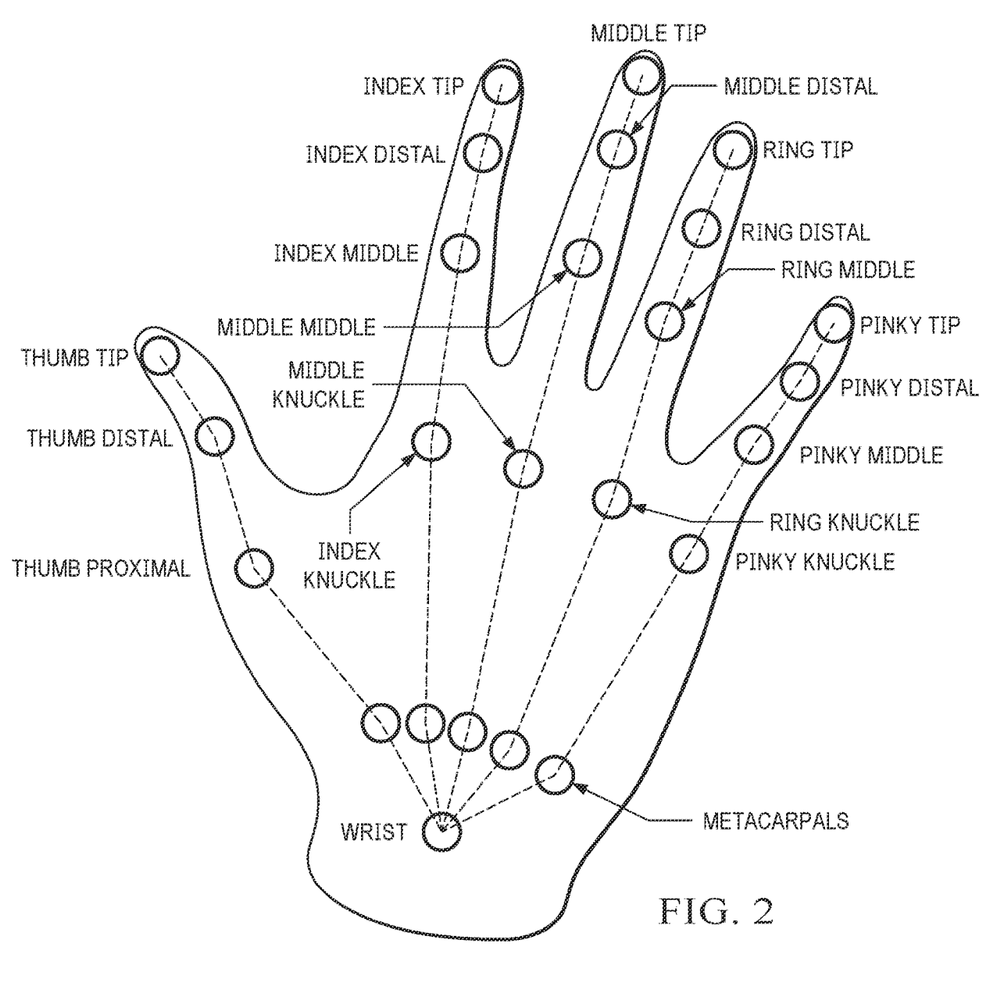
FIG. 2 depicts the various joints of a human hand.

FIG. 1 shows an example of a virtual stethoscope 100 that can be placed in the user's hands during the auscultation stage of an examination. The stethoscope 100 of FIG. 1 is represented visually by a 3D model of a wireless stethoscope. The position of the stethoscope is set to track and line up with the augmented reality system user's hand middle middle joint (see the diagram of FIG. 2, which shows various joints of a human hand). Other configurations of virtual instruments and orientations are also possible. In some embodiments, if the user's hand cannot be found by the hand tracking system, the stethoscope will disappear. The virtual stethoscope has a collider used to detect if it hits an auscultation sound point (described below) and an audio listener component to be used as the source to receive sound in the 3D space.

Figure 3:
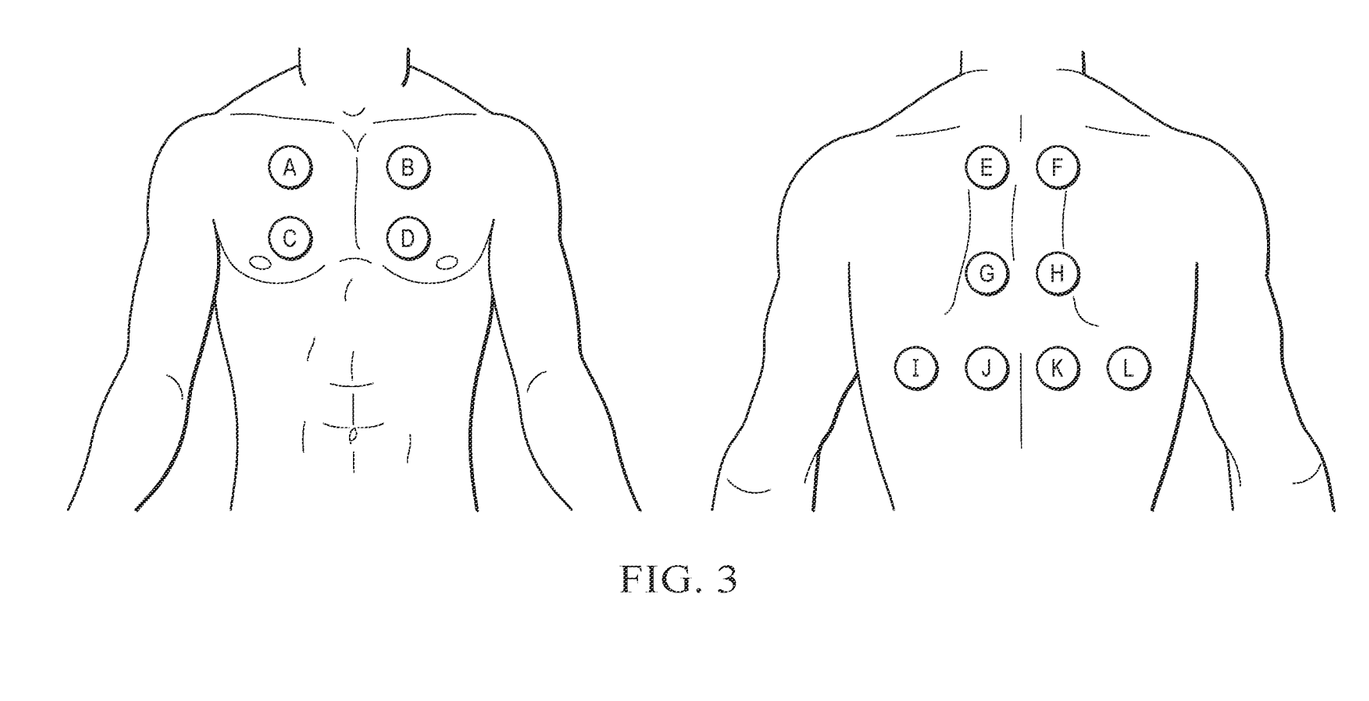
FIG. 3 depicts front and rear views of a human with locations of exemplary auscultation sound points.
Figure 4:
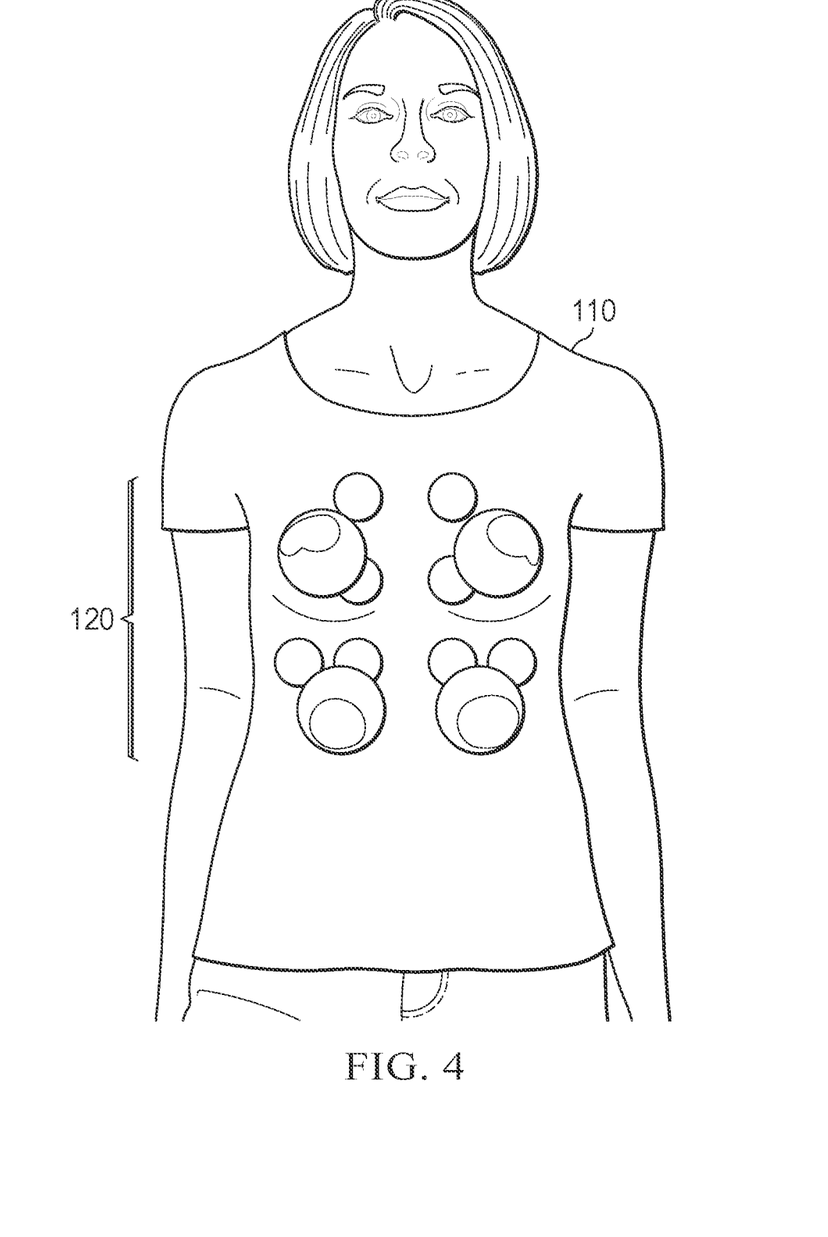
FIG. 4 depicts a 3D representation of a virtual patent showing a plurality of auscultation sound points represented by spheres.

The system is configured to enable various auscultation sound points for generating sounds based on the location of the virtual stethoscope and the parameters configured for the virtual patent. FIG. 3 shows front and rear views of a human with locations of exemplary auscultation sound points (labeled A-L). FIG. 4 shows a 3D representation of a virtual patent 110 showing a plurality of auscultation sound points 120 represented by spheres. The auscultation sound point locations on the patient shown in the figures are usually invisible to the user to enhance training.

In the example of FIGS. 3-4, the auscultation sound points 120 are a group of 12 invisible spheres attached to the virtual patient's chest and back. Each auscultation sound point can be assigned a sound file to play, which can be heard if the stethoscope is in range of that point. The sounds from different auscultation sound points can overlap and have a minimum and maximum range with a rolloff (for example, linear, exponential, etc.) of sound volume between the min and max range. The resulting sounds heard by the user can therefore be a blend of sounds from multiple sound points based on the distance to the respective sound points. In other words, several auscultation zones are mapped to the patient models (e.g., see FIG. 4) and the system interprets the position of the user's hand in relation to the auscultation zones. The system will play a sound based on where the user's hand is in relation to a given zone, and will blend the sound from adjacent zones. For example, in the example of a virtual patient configured to have a crackle in one part of the lung, the crackle will get louder as the user gets closer to the source of the crackle.

Figure 5:
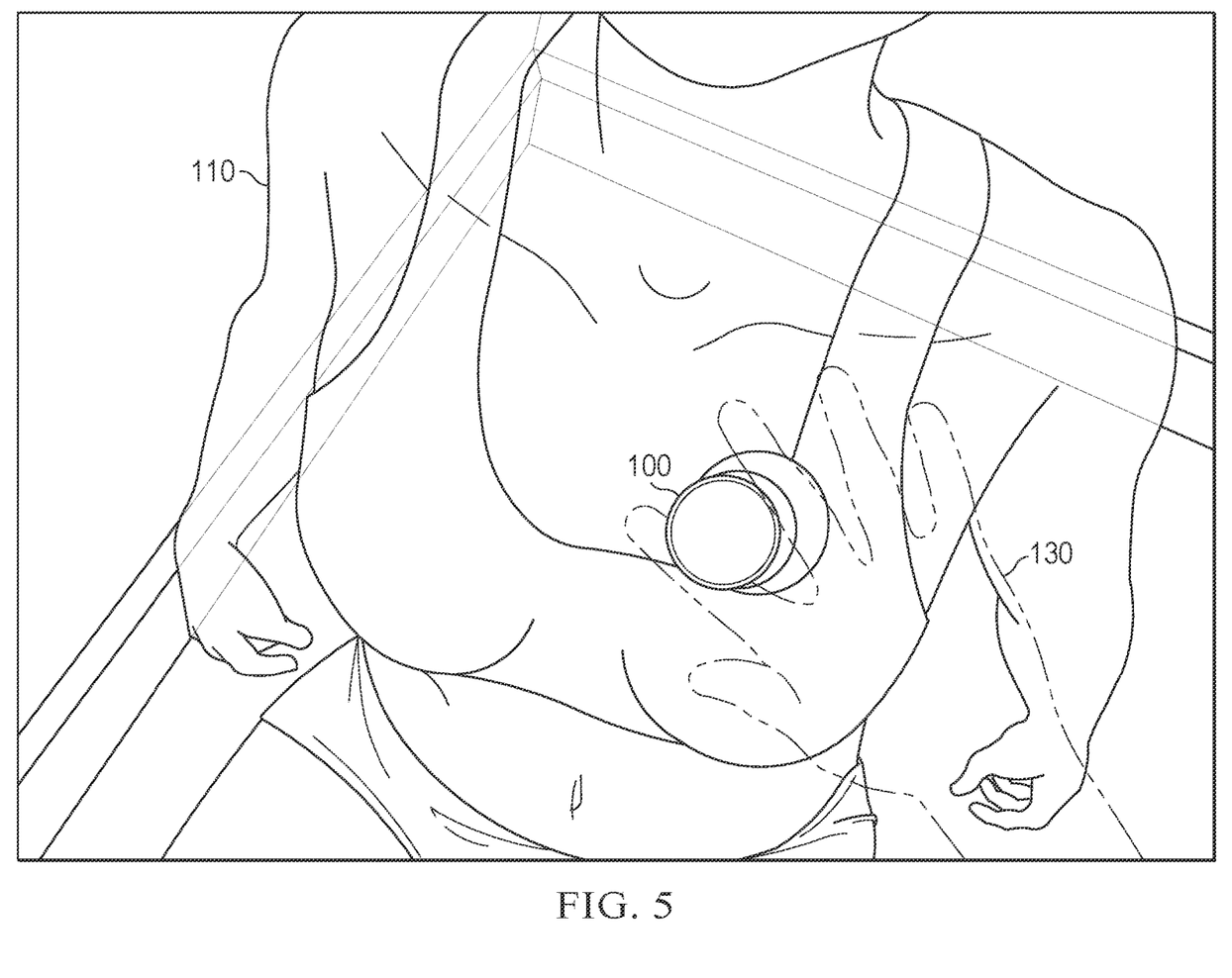
FIGS. 5-6 depict examples of what a user of an augmented reality device will see when conducting the auscultation stage of a physical examination.
Figure 6:
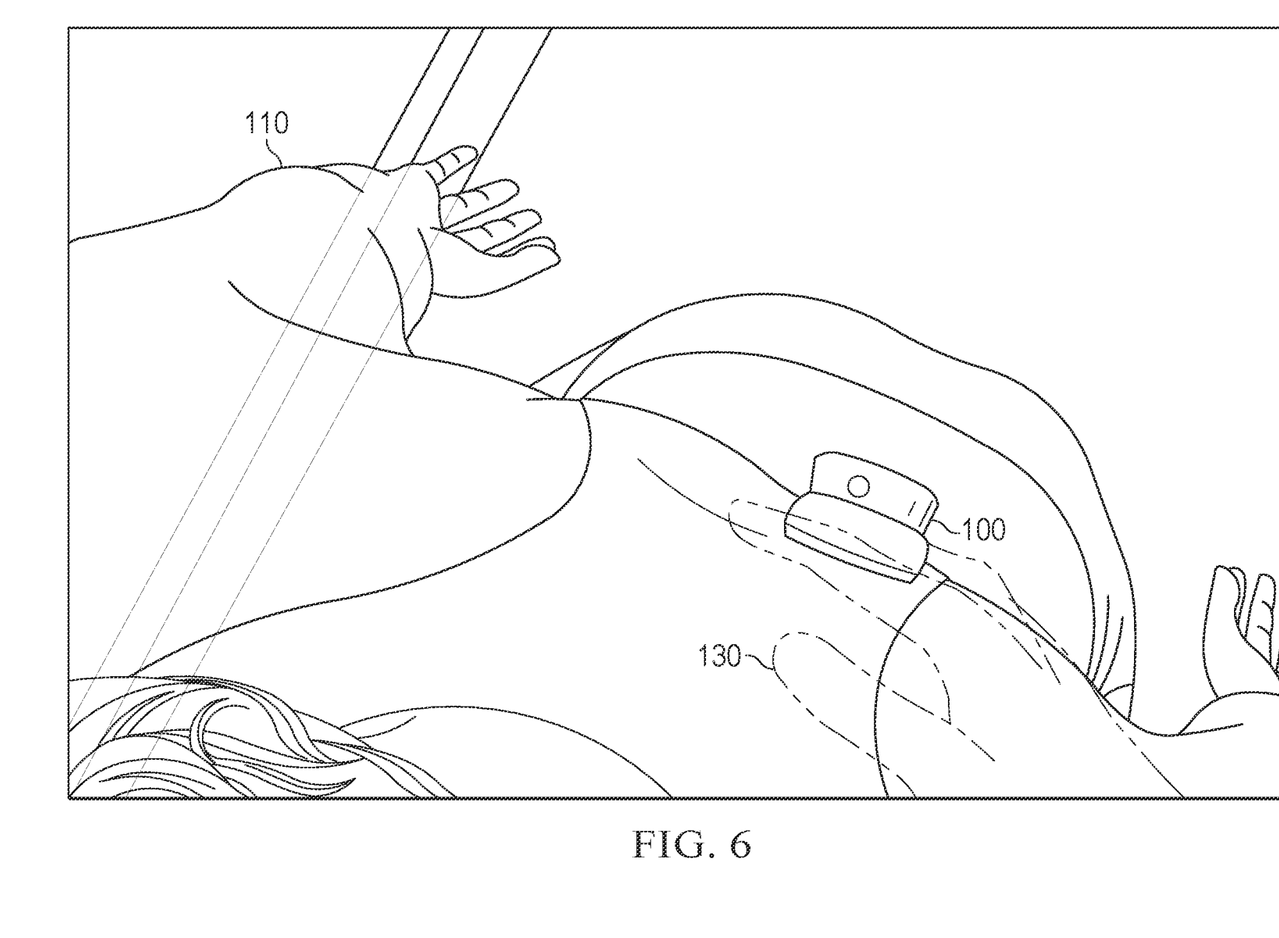

In some embodiments of an auscultation examination, the user wearing a Hololens 2 device (or similar augmented reality device) can start up an "Auscultation Exam" application, which will make a virtual stethoscope appear on their hand. The user can move the stethoscope around with their hand, as described above. The user can put the stethoscope up to the virtual patient's chest or back to hear auscultation sounds, based on the configuration of the auscultation sound points and patient configuration (described above). In this manner, the user (e.g., a medical trainee) can be trained to examine a patient in a more efficient and more realistic manner than is possible with prior art systems. In one example, the system may use approximately 30-50 sound files for auscultation simulation, although any desired number may be used. FIGS. 5-6 show examples of what a user of an augmented reality device will see when conducting the auscultation stage of a physical examination. As shown, the user can position the virtual stethoscope 100 where desired on the virtual patient. The user will hear auscultation sounds based on the position of the virtual stethoscope. Note that with a real stethoscope, a user hears sounds from the perspective of the resonator of the stethoscope, not from the perspective of the location of the user's ears. Therefore, with the virtual stethoscope, the sound provided to the user can be the sound from the perspective of the resonator of the virtual stethoscope. Depending on the augmented reality system used, applications may have to be configured to change the observation perspective of the sounds from the user's ears to the resonator of the virtual stethoscope. In one example, an audio listener software component can be located to any desired position in the virtual space.

Palpation and percussion maneuvers of a physical examination are conducted in a similar manner, without the virtual stethoscope. For example, a "Palpation Exam" application will enable a user to position their hands 130 on the virtual patent to check for areas of tenderness, etc. In response to the user's actions, the virtual patent 110 can react accordingly, as one skilled in the art would understand. In some embodiments, a virtual patent 110 can have 4-9 mappable spaces on the patient's abdomen, although more or less mappable spaces are also possible. When a user places or pushes their hand 130 on the abdomen, the system will detect that "collision." In one example, as a user pushes, the system will detect how far the user pushes. In one example, once the user pushes far enough, the virtual patient 110 will respond/react to the palpation. For example, when pressing on a location with tenderness, the virtual patient 110 may react (e.g., by saying "ouch"). Similarly, with rebound tenderness, when the user removes their hand 130, the patent will also react accordingly. The configured reactions can vary depending on any desired factors, such as the collision direction, velocity, and depth of the hand. If desired, the appearance of the virtual patient can vary based on the user's interactions. For example, during a palpation stage of an exam, the patient model can show the indentation resulting from the palpation.

Figure 7A:
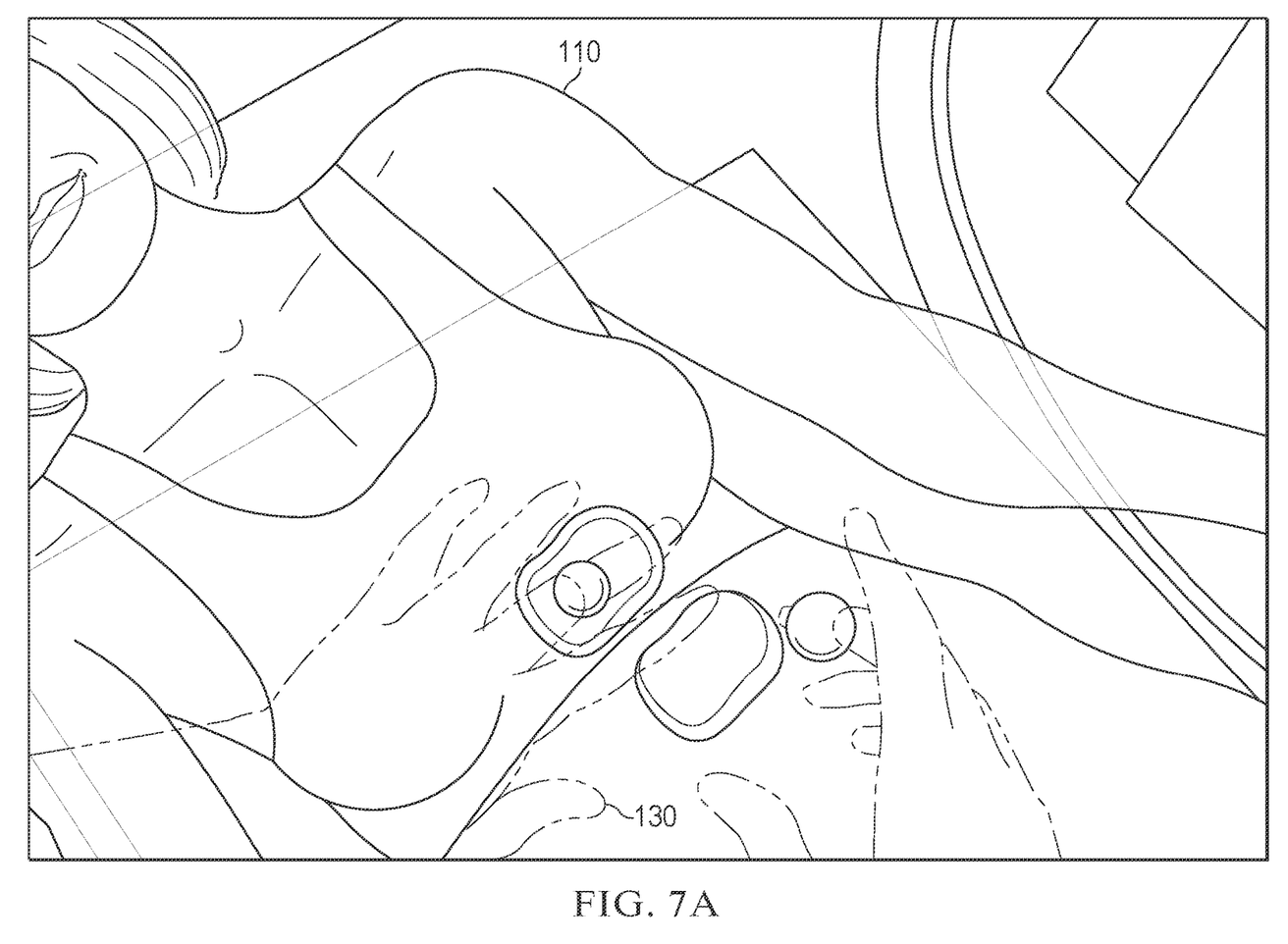
FIGS. 7A-7B depict an example of what a user of an augmented reality device will see when conducting a percussion auscultation stage of a physical examination.
Figure 7B:
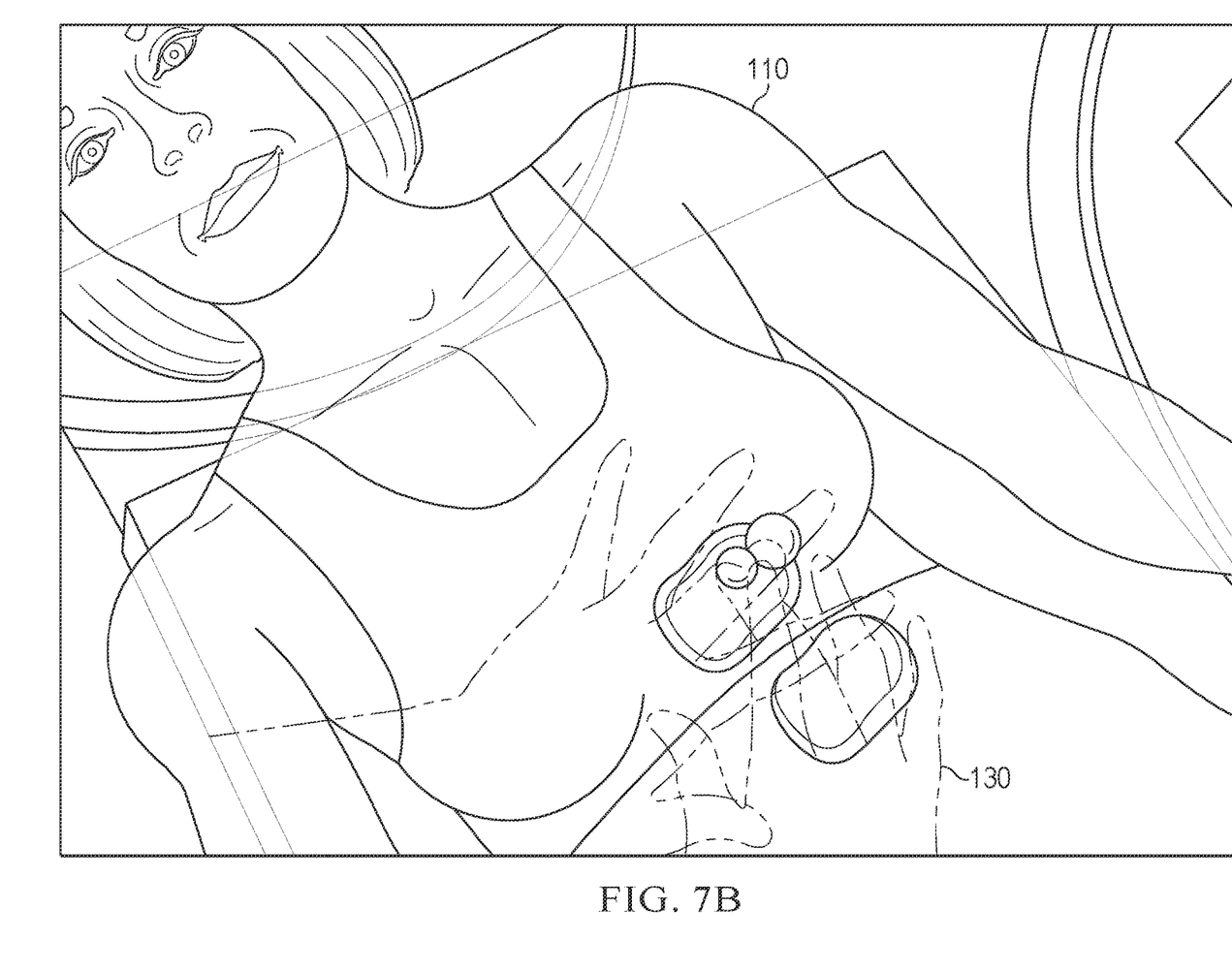

In the example of a "Percussion Exam" application, a user can conduct a percussion stage, for example, by touching the virtual patent 110 and using their other hand 130 to tap the hand 130 placed on the virtual patient. In response to the user's actions, the system can generate responsive sounds. FIGS. 7A-7B show an example of what a user of an augmented reality device will see when conducting the percussion auscultation stage of a physical examination. As shown in FIG. 7A, the user can pace one hand 130 on the virtual patient, and then tap that hand with their other hand (FIG. 7B). The user will hear sounds based on the location and intensity of the collision, as well as the virtual patient configuration. In some examples, the augmented reality system tracks the velocity of the taps and sounds are mapped based on the velocity and location of the collision. The virtual patient 110 can be configured as desired. In one example, the virtual patient 110 can be configured for percussion actions primarily in the thorax of the patient. In one example, the system may use approximately 6 sound files for percussion simulation, although any desired number may be used. Other types of physical examination stages can also be configured and performed by the invention, as one skilled in the art would understand.

Figure 8:
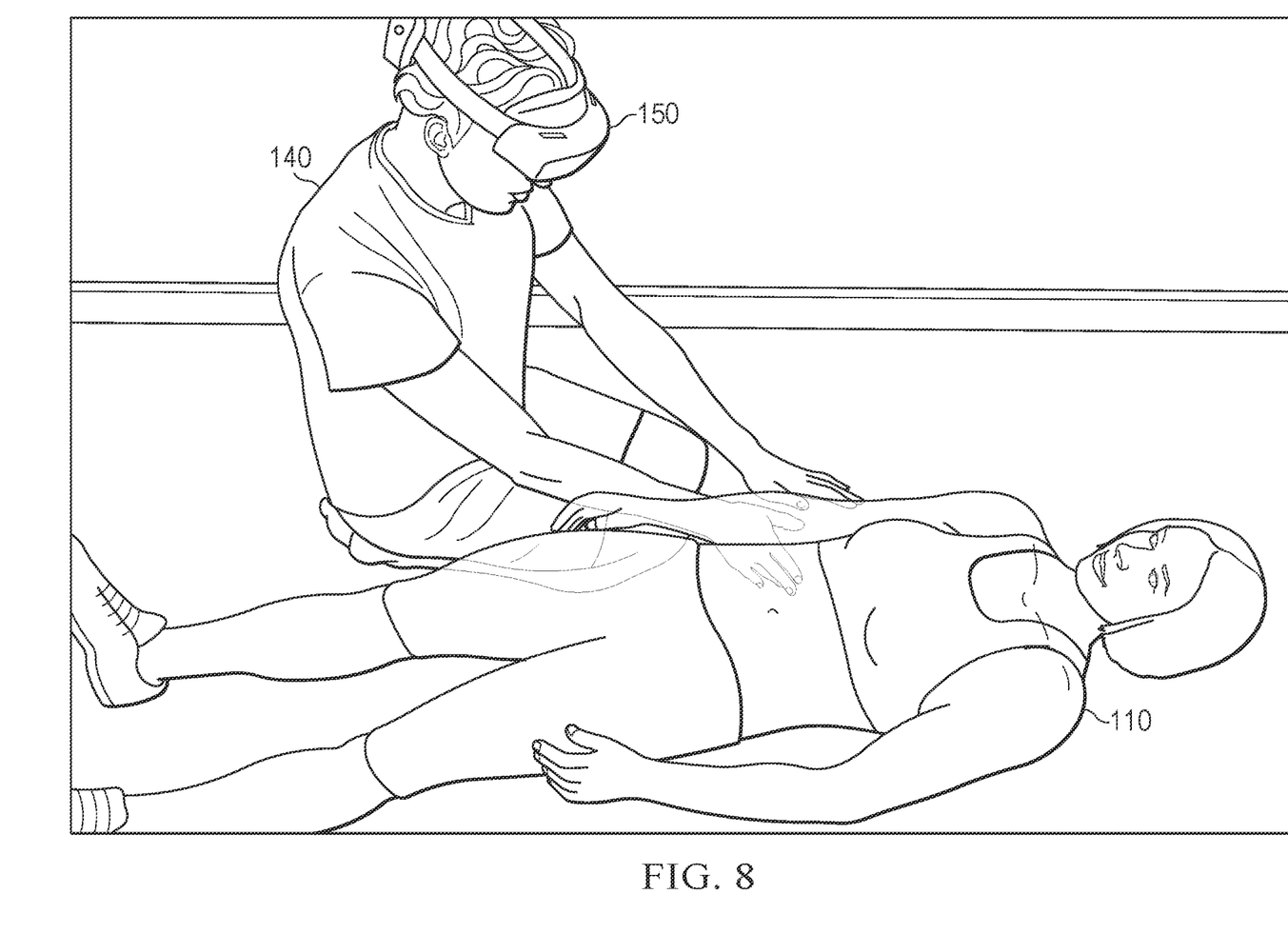
FIG. 8 depicts a user of an augmented reality device interacting with a virtual patient.

While FIGS. 5-7 show the virtual patient from the perspective of a user of an augmented reality device, FIG. 8 shows the user and virtual patient from a third person perspective (although note that the virtual patient would not be visible to a person without an augmented reality device). FIG. 8 is a view of user 140 (e.g., a medical trainee, etc.) of an augmented reality device 150 interacting with a virtual patient 110, such as that shown in FIGS. 5-7.

While several examples are provided above for types of examinations or procedures that can be performed, note that numerous other types of examinations are also possible, such as neuro examples, the manipulation of limbs, etc. In one example, a user can take a knee joint of a virtual patient through a range of motion looking for pain or other reactions of the virtual patient. In another example, a user can move the head of a virtual patient around, while looking at the response of the eyes of the virtual patient. Numerous other examples of manipulating a body part through a given range of motion looking for manifestations of disease are also possible, as one skilled in the art would understand.

Figure 9:
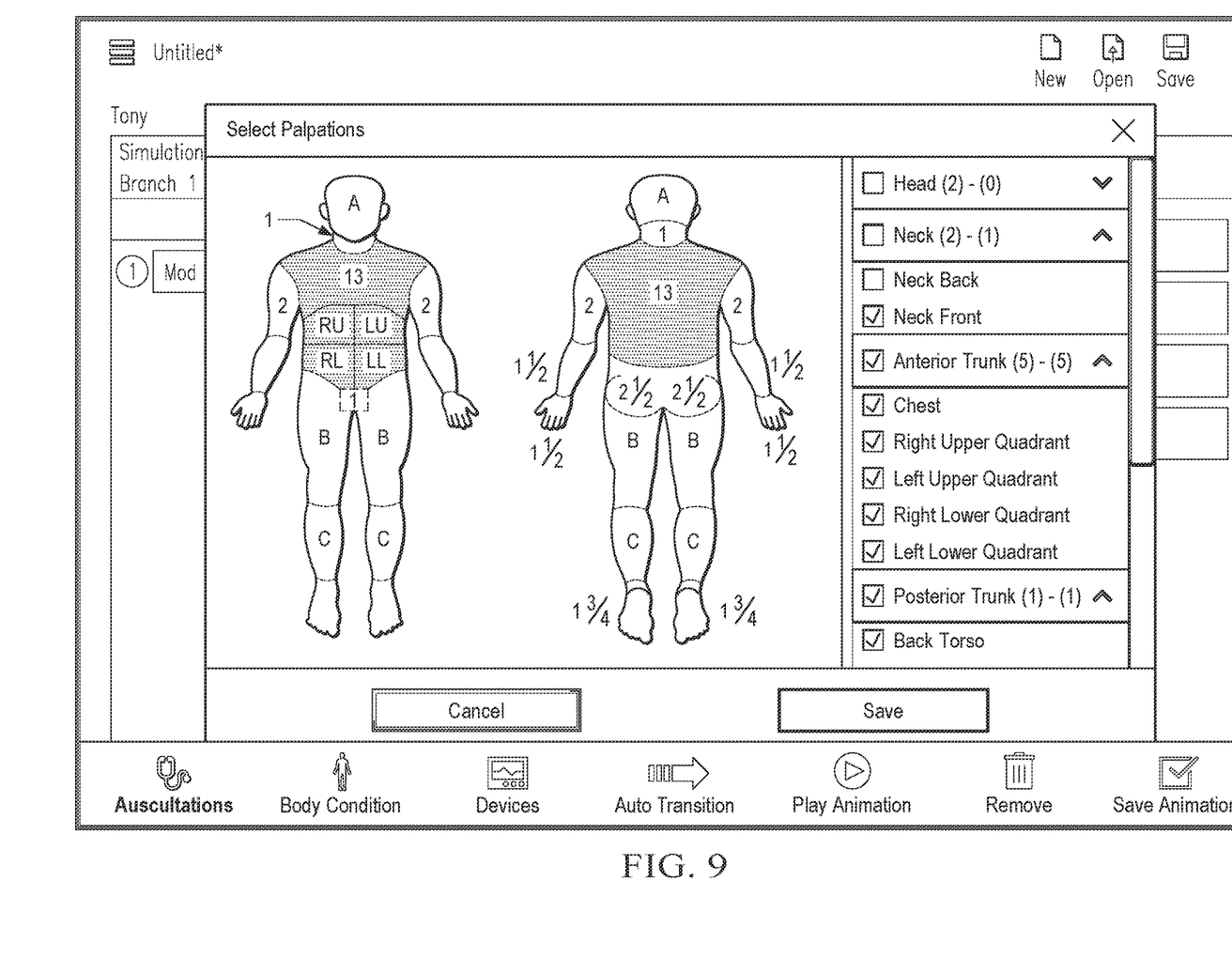
FIG. 9 is an exemplary screenshot of a controller editor screen showing the user interface (UI) for the palpation editor.

The system may also include an expanded editor or builder application. The system described above may include controller (which includes a scenario editor capability), and/or builder applications to create and configure simulations with multiple patient states. For example, in some embodiments, each patient state can have auscultation group data assigned to it. In some examples, there can be several default auscultation group options available to choose from and assign to each patient state. Auscultation group data may be a group of 12 sound files which map to each of the 12 auscultation sound points on the virtual patient (described above). Similar editor and/or builder functions are available for other types of physical exams (e.g., palpation, percussion, etc.). FIG. 9 is an exemplary screenshot of a controller editor screen, with a designer viewing configuration options for a palpation stage. In FIG. 9, the UI allows a designer to select palpation locations.

In some examples, the builder application can be a web application that may be used similarly to the Controller application, to create simulations with patient states with auscultations data assigned. The difference being that in the Builder app, the user can pick a sound for each individual auscultation sound point in the group and can also upload their own sounds to use.

Those skilled in the relevant art will appreciate that the invention can be implemented or practiced with other computer system configurations, including without limitation multi-processor systems, network devices, mini-computers, mainframe computers, data processors, and the like. The invention can be embodied in a general purpose computer, or a special purpose computer or data processor that is specifically programmed, configured, or constructed to perform the functions described in detail herein. The invention can also be employed in distributed computing environments, where tasks or modules are performed by remote processing devices, which are linked through a communications network such as a local area network (LAN), wide area network (WAN), and/or the Internet. In a distributed computing environment, program modules or subroutines may be located in both local and remote memory storage devices. These program modules or subroutines may, for example, be stored or distributed on computer-readable media, including magnetic and optically readable and removable computer discs, stored as firmware in chips, as well as distributed electronically over the Internet or over other networks (including wireless networks). Example chips may include Electrically Erasable Programmable Read-Only Memory (EEPROM) chips. Embodiments discussed herein can be implemented in suitable instructions that may reside on a non-transitory computer readable medium, hardware circuitry or the like, or any combination and that may be translatable by one or more server machines. Examples of a non-transitory computer readable medium are provided below in this disclosure.

ROM, RAM, and HD are computer memories for storing computer-executable instructions executable by the CPU or capable of being compiled or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" is not limited to ROM, RAM, and HD and can include any type of data storage medium that can be read by a processor. Examples of computer-readable storage media can include, but are not limited to, volatile and non-volatile computer memories and storage devices such as random access memories, read-only memories, hard drives, data cartridges, direct access storage device arrays, magnetic tapes, floppy diskettes, flash memory drives, optical data storage devices, compact-disc read-only memories, and other appropriate computer memories and data storage devices. Thus, a computer-readable medium may refer to a data cartridge, a data backup magnetic tape, a floppy diskette, a flash memory drive, an optical data storage drive, a CD-ROM, ROM, RAM, HD, or the like.

The processes described herein may be implemented in suitable computer-executable instructions that may reside on a computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including C, C++, Java, JavaScript, HTML, or any other programming or scripting code, etc. Other software/hardware/network architectures may be used. For example, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or code an of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more general purpose digital computers, by using application specific integrated circuits, programmable logic devices, field programmable gate arrays, optical, chemical, biological, quantum or nanoengineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory. Such computer-readable medium shall generally be machine readable and include software programming or code that can be human readable (e.g., source code) or machine readable (e.g., object code). Examples of non-transitory computer-readable media can include random access memories, read-only memories, hard drives, data cartridges, magnetic tapes, floppy diskettes, flash memory drives, optical data storage devices, compact-disc read-only memories, and other appropriate computer memories and data storage devices. In an illustrative embodiment, some or all of the software components may reside on a single server computer or on any combination of separate server computers. As one skilled in the art can appreciate, a computer program product implementing an embodiment disclosed herein may comprise one or more non-transitory computer readable media storing computer instructions translatable by one or more processors in a computing environment.

A "processor" includes any, hardware system, mechanism or component that processes data, signals or other information. A processor can include a system with a general-purpose central processing unit, multiple processing units, dedicated circuitry for achieving functionality, or other systems. Processing need not be limited to a geographic location or have temporal limitations. For example, a processor can perform its functions in "real-time," "offline," in a "batch mode," etc. Portions of processing can be performed at different times and at different locations, by different (or the same) processing systems.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, a term preceded by "a" or "an" (and "the" when antecedent basis is "a" or "an") includes both singular and plural of such term, unless clearly indicated otherwise (i.e., that the reference "a" or "an" clearly indicates only the singular or only the plural). Also, as used in the description herein, the meaning of "in" includes "in" and "on" unless the context clearly dictates otherwise.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

What is claimed is:

1. A system comprising:
   an augmented reality display device having a controller, the augmented reality device configured to:
   generate a display of a virtual patient;
   track the hands of a user to enable the user to perform one or more physical examinations on the virtual patient; and
   responsive to the tracking the hands of the user during the performance of the one or more physical examinations on the virtual patient, generate one or more simulated audio or visual reactions by the virtual patient that can be perceived by the user while viewing the virtual patient via the generated display to simulate reactions of a real patient undergoing a similar physical examination based on one or more of collision direction, velocity, and depth of the hand of the user relative to the virtual patient.

2. The system of claim 1, wherein the one or more physical examinations on the virtual patient includes auscultation.

3. The system of claim 2, wherein the controller device is further configured to provide a virtual stethoscope controllable by the user.

4. The system of claim 2, wherein the controller device is further configured to:
   provide a plurality of auscultation sound points on the virtual patent; and
   responsive to the user's hand being in the proximity of one or more of the auscultation sound points, generating the response by the virtual patient that can be perceived by the user.

5. The system of claim 1, wherein the one or more physical examinations on the virtual patient includes palpation.

6. The system of claim 1, wherein the one or more physical examinations on the virtual patient includes percussion.

7. The system of claim 1, wherein the one or more physical examinations on the virtual patient includes allowing the user to manipulate a virtual body part through a given range of motion and observe a reaction of the virtual patient.

8. A method of simulating a medical examination comprising:
configuring an augmented reality display device to display a virtual patient;
tracking the hands of a user to enable the user to perform one or more physical examinations on the virtual patient; and
responsive to the tracking the hands of the user during the performance of the one or more physical examinations on the virtual patient, generating one or more simulated audio or visual reactions by the virtual patient that can be perceived by the user while viewing the virtual patient via the generated display to simulate reactions of a real patient undergoing a similar physical examination based on one or more of collision direction, velocity, and depth of the hand of the user relative to the virtual patient.

9. The method of claim 8, wherein the one or more physical examinations on the virtual patient includes auscultation.

10. The method of claim 9, further comprising providing a virtual stethoscope controllable by the user.

11. The method of claim 9, further comprising:
providing a plurality of auscultation sound points on the virtual patent; and
responsive to the user's hand being in the proximity of one or more of the auscultation sound points, generating the response by the virtual patient that can be perceived by the user.

12. The method of claim 8, wherein the one or more physical examinations on the virtual patient includes palpation.

13. The method of claim 8, wherein the one or more physical examinations on the virtual patient includes percussion.

14. The method of claim 8, wherein the one or more physical examinations on the virtual patient includes allowing the user to manipulate a virtual body part through a given range of motion and observe a reaction of the virtual patient.

15. A method of training a user to conduct physical examinations comprising:
providing the user with an augmented reality display device;
configuring the augmented reality display device to display a virtual patient;
tracking the hands of the user to enable the user to perform one or more physical examinations on the virtual patient; and
responsive to the tracking the hands of the user during the performance of the one or more physical examinations on the virtual patient, generating one or more simulated audio or visual reactions by the virtual patient that can be perceived by the user while viewing the virtual patient via the generated display to simulate reactions of a real patient undergoing a similar physical examination based on one or more of collision direction, velocity, and depth of the hand of the user relative to the virtual patient.

16. The method of claim 15, wherein the one or more physical examinations on the virtual patient includes auscultation.

17. The method of claim 16, further comprising providing a virtual stethoscope controllable by the user.

18. The method of claim 16, further comprising:
providing a plurality of auscultation sound points on the virtual patent; and
responsive to the user's hand being in the proximity of one or more of the auscultation sound points, generating the response by the virtual patient that can be perceived by the user.

19. The method of claim 15, wherein the one or more physical examinations on the virtual patient includes palpation.

20. The method of claim 15, wherein the one or more physical examinations on the virtual patient includes percussion.

* * * * *